(12) United States Patent
Wen et al.

(10) Patent No.: US 8,494,269 B2
(45) Date of Patent: Jul. 23, 2013

(54) METHOD AND SYSTEM FOR SCREENING OF A TO-BE-ANALYZED CANDIDATE AS A SKIN-WHITENING AGENT

(75) Inventors: Zhi-Hong Wen, Kaohsiung (TW);
Po-Shien Wu, Kaohsiung (TW);
Wen-Sheng Liu, Kaohsiung (TW);
Fu-Hsin Chang, Kaohsiung (TW);
Tsung-Wei Chen, Kaohsiung (TW)

(73) Assignee: National Sun Yat-Sen University, Kaohsiung (TW)

( * ) Notice: Subject to any disclaimer, the term of this patent is extended or adjusted under 35 U.S.C. 154(b) by 501 days.

(21) Appl. No.: 12/940,576

(22) Filed: Nov. 5, 2010

(65) Prior Publication Data
US 2011/0129136 A1    Jun. 2, 2011

(30) Foreign Application Priority Data
Nov. 9, 2009    (TW) ................ 98137923 A

(51) Int. Cl.
*G06K 9/00*    (2006.01)
(52) U.S. Cl.
USPC .......................... 382/181; 382/100
(58) Field of Classification Search
USPC ................. 382/181, 231
See application file for complete search history.

(56) References Cited

U.S. PATENT DOCUMENTS

2008/0240527 A1*    10/2008    Keller ................... 382/128
2010/0119119 A1*    5/2010    Rittscher et al. ........... 382/110

OTHER PUBLICATIONS

Choi, Tae-Young et al.; Zebrafish as a new model for photype-based screening of melanogenic regulatory compounds; Pigment Cell & Melanoma Research; 2007; 20:120-127.

* cited by examiner

*Primary Examiner* — Edward Park

(57) ABSTRACT

A method for screening of a to-be-analyzed candidate as a skin-whitening agent, includes the steps of: (a) setting a first feature parameter corresponding to a first group of zebrafish that are bred under a predetermined set of breeding conditions; (b) administering the to-be-analyzed candidate to a second group of zebrafish that are bred under the predetermined set of breeding conditions; (c) capturing images of the zebrafish in the second group; (d) determining, from the images captured in step (c), a second feature parameter corresponding to the second group of zebrafish; and (e) concluding that the to-be-analyzed candidate is suitable as a skin-whitening agent if a difference between the first and second feature parameters has statistical significance. A system for implementing the method is also disclosed.

11 Claims, 11 Drawing Sheets

METHOD AND SYSTEM FOR SCREENING OF A TO-BE-ANALYZED CANDIDATE AS A SKIN-WHITENING AGENT

CROSS-REFERENCE TO RELATED APPLICATION

This application claims priority of Taiwanese Application No. 098137923, filed on Nov. 9, 2009.

BACKGROUND OF THE INVENTION

1. Field of the Invention

The invention relates to a method and a system for screening of a to-be-analyzed candidate as a skin-whitening agent.

2. Description of the Related Art

For the characteristics that they produce opticallly transparent embryos and that embryo development is rapid, zebrafish, which is a tropical freshwater fish with a binominal name of *Danio Rerio*, is considered an important vertebrate model organism in scientific research, such as in the fields of molecular genetics and developmental biology.

Since melanin pigment is inherently present in the body surface of zebrafish, no complex preparation procedure is necessary to induce melanogenesis for experimental purposes. Furthermore, since zebrafish has the advantages of being low-cost, small-sized (thus taking less space) and easily-bred, of having a fully-sequenced genetic code, and of requiring little test dosage during experimentation, the use of zebrafish as an in vivo model for screening of a to-be-analyzed candidate as a skin-whitening agent has gained increasing attention.

In the article by T. Y. Choi et al. and entitled "Zebrafish as a new model for phenotype-based screening of melanogenic regulatory compounds", *Pigment Cell & Melanoma Research,* 2007, 20:120-127, the content of which is incorporated herein by reference, a method for screening of melanogenic regulatory compounds is disclosed to include the following steps. (1) Synchronized embryos were collected and dispensed in 96-well plates containing 200 μL embryo medium. (2) Test compounds were dissolved in 0.1% dimethyl sulfoxide (DMSO), and were then added to the embryo medium at 9 hour post-fertilization for 63 hours of exposure time. (3) 0.2 mM of 1-phenyl-2-thiourea (PTU) was used to generate transparent zebrafish without interfering with the developmental process as a standard positive control. (4) For observation, embryos were dechorionated by forceps, anesthetized in tricaine methanesulfonate solution, mounted in 3% methyl cellulose on a depression slide, and photographed under the stereomicroscope MZ16 (Leica). (5) The effects on the pigmentation of zebrafish were scored arbitrarily by the naked eye as follows: none or mild, <10%; moderate, 10-49%; profound, >50%.

Although the conventional method demonstrated the use of zebrafish for the screening of melanogenic regulatory compounds, it fails to obtain objective, reliable, and statistically significant results due to reliance upon the naked eye as a basis for determination.

SUMMARY OF THE INVENTION

Therefore, the object of the present invention is to provide a method and a system for screening of a to-be-analyzed candidate as a skin-whitening agent that provides accurate and objective results.

According to one aspect of the present invention, there is provided a method for screening of a to-be-analyzed candidate as a skin-whitening agent. The method includes the steps of:

(a) setting a first feature parameter corresponding to a first group of zebrafish that are bred under a predetermined set of breeding conditions;

(b) administering the to-be-analyzed candidate to a second group of zebrafish that are bred under the predetermined set of breeding conditions;

(c) capturing images of the zebrafish in the second group;

(d) determining, from the images captured in step (c), a second feature parameter corresponding to the second group of zebrafish; and (e) concluding that the to-be-analyzed candidate is suitable as a skin-whitening agent if a difference between the first and second feature parameters has statistical significance.

According to another aspect of the present invention, there is provided a system for screening of a to-be-analyzed candidate as a skin-whitening agent. The system includes an image acquisition unit, an image analyzing unit and a processing unit. The image acquisition unit is for acquiring images of zebrafish of first and second groups. The first group of zebrafish is bred under a predetermined set of breeding conditions. The second group of zebrafish is bred under the predetermined set of breeding conditions and is administered with the to-be-analyzed candidate during the breeding process. The image analyzing unit is for determining, from the images acquired by the image acquisition unit, a first feature parameter corresponding to the first group of zebrafish and a second feature parameter corresponding to the second group of zebrafish. The processing unit is for concluding that the to-be-analyzed candidate is suitable as a skin-whitening agent if a difference between the first and second feature parameters has statistical significance.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
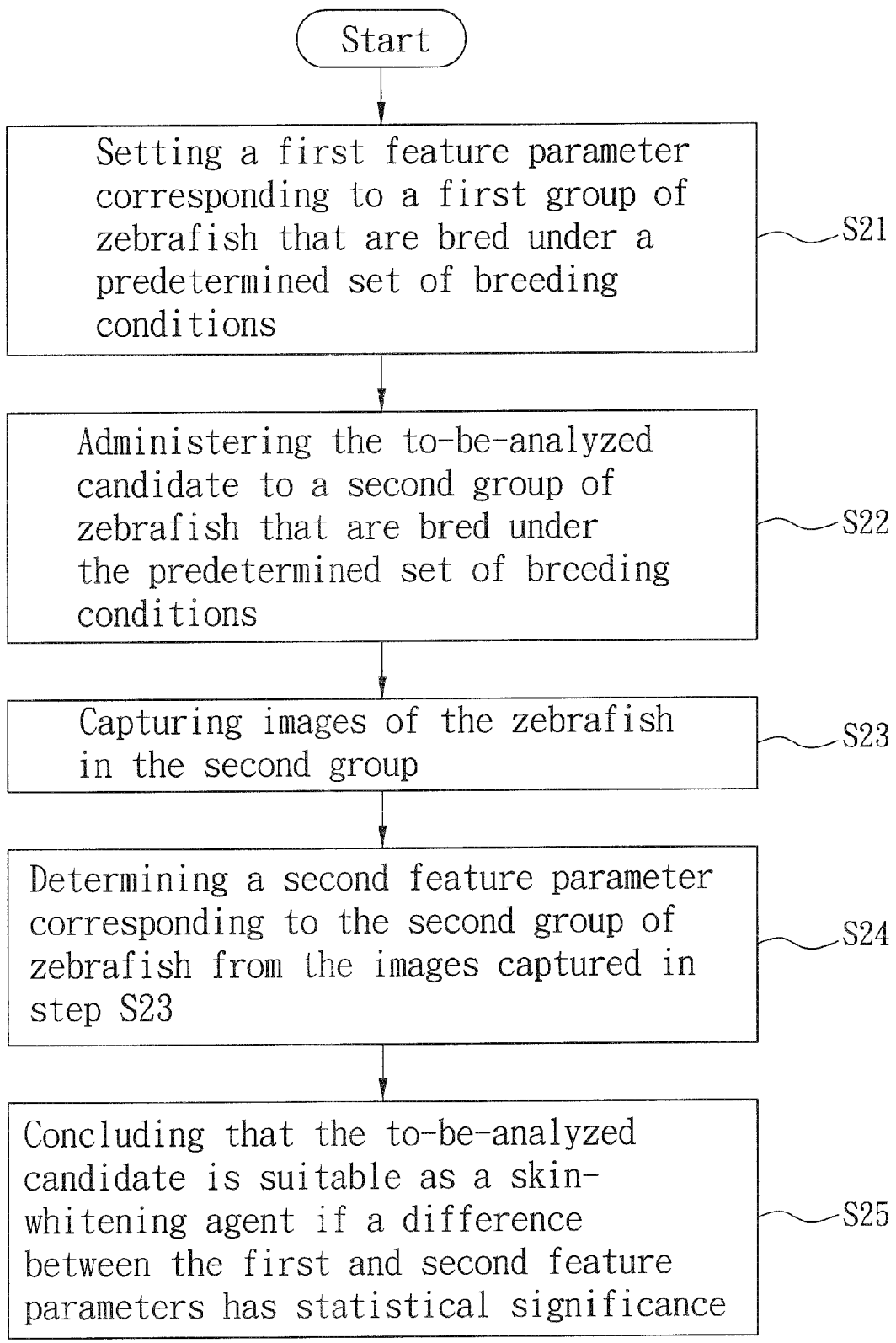
FIG. 1 is a flow chart, illustrating the preferred embodiment of a method for screening of a to-be-analyzed candidate as a skin-whitening agent according to the present invention.

With reference to FIG. 1, the preferred embodiment of a method for screening of a to-be-analyzed candidate as a skin-whitening agent according to the present invention includes the following steps.

In step S21, a first feature parameter is set corresponding to a first group of zebrafish that are bred under a predetermined set of breeding conditions.

In step S22, the to-be-analyzed candidate is administered to a second group of zebrafish that are bred under the predetermined set of breeding conditions.

In this embodiment, the predetermined set of breeding conditions includes a controlled breeding temperature of 28.5 degrees Celsius, and a light-dark cycle of 14 hours of light and 10 hours of darkness. According to the present invention, each of the first and second groups of zebrafish may be fish larvae or adult fish, and may come from the same parental generation or different parental generations. Preferably, when using zebrafish larvae for the screening of the to-be-analyzed candidate, the larva zebrafish is bred from a fertilized egg for 57 hours under the predetermined breeding conditions.

According to the present invention, the to-be-analyzed candidate may be a pure compound, such as arbutin, N-phenylthiourea (PTU), kojic acid, linoleic acid, α-linoleic acid, hydroquinone, ascorbic acid, azelaic acid, phytic acid, and haginin A, etc., or may be a composition, such as extracts of *Lespedeza cyrtobotrya* and extracts of *Podocarpus* sp., etc.

In step S23, images of the zebrafish in the second group are captured. In this embodiment, step S23 is implemented using a microscope that is equipped with a digital camera.

In step S24, a second feature parameter corresponding to the second group of zebrafish is determined from the images captured in step S23.

In step S25, it is concluded that the to-be-analyzed candidate is suitable as a skin-whitening agent if a difference between the first and second feature parameters has statistical significance. Preferably, in step S25, the difference between the first and second feature parameters is determined to have statistical significance when a p-value resulting from the difference is smaller than 0.05.

Figure 2:
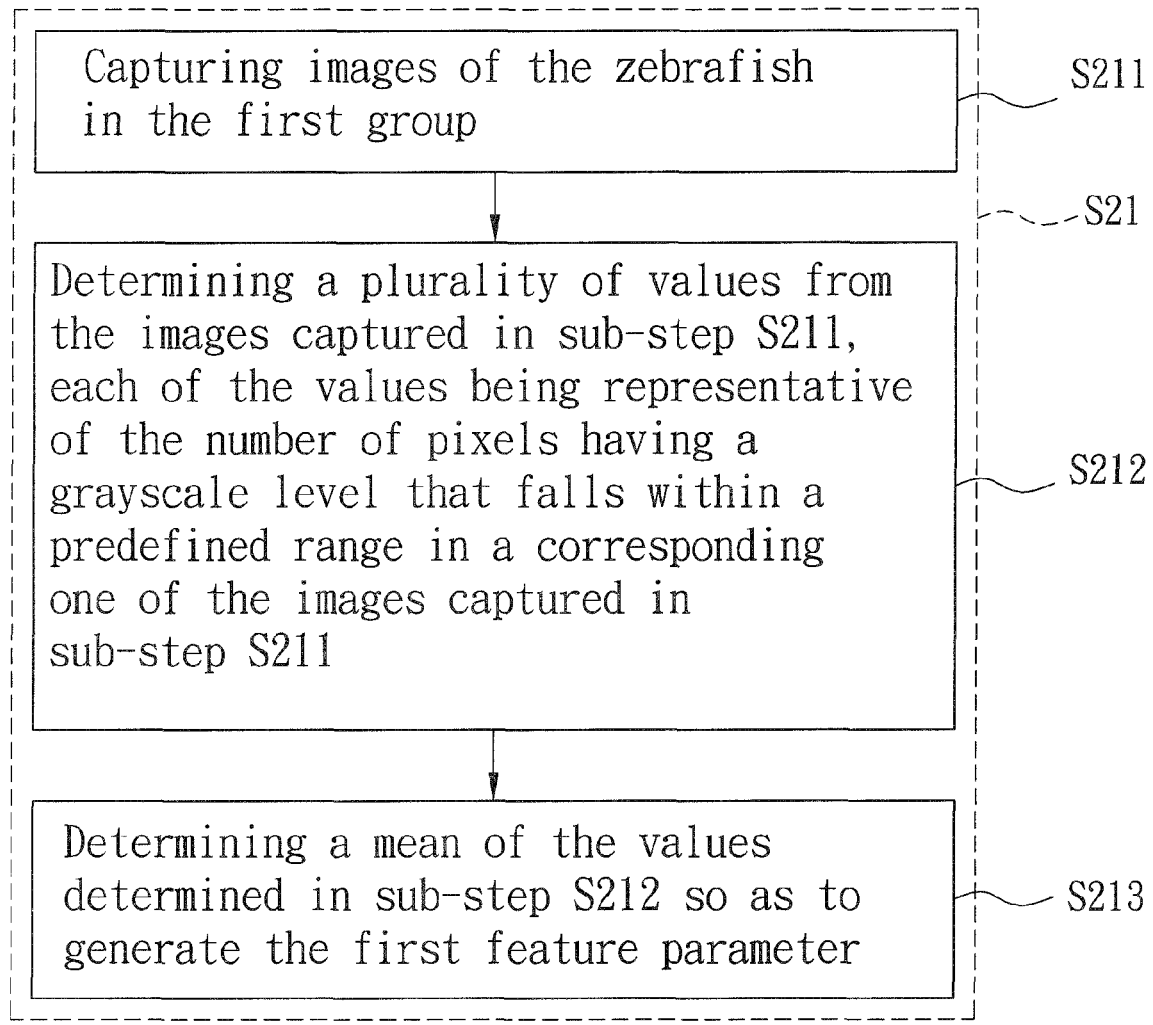
FIG. 2 is a flow chart, illustrating sub-steps of setting a first feature parameter.

With reference to FIG. 2, step 21 of this embodiment includes the following sub-steps. In sub-step S211, images of the zebrafish in the first group are captured. In sub-step S212, a plurality of values are determined from the images captured in sub-step S211. Each of the values is representative of the number of pixels having a grayscale level that falls within a predefined range in a corresponding one of the images captured in sub-step S211. In sub-step S213, a mean of the values determined in sub-step S212 is determined so as to obtain the first feature parameter. It should be noted herein that the present invention also encompasses those implementations where the first feature parameter is standardized and preset.

Figure 3:
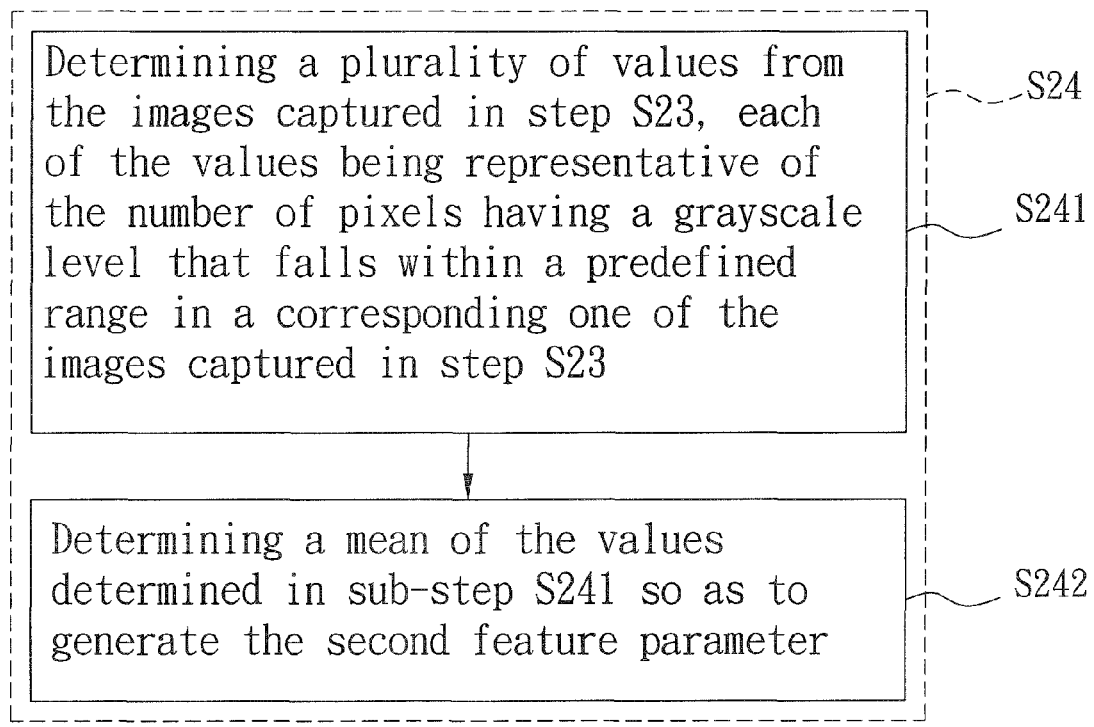
FIG. 3 is a flow chart, illustrating sub-steps of determining a second feature parameter.

With reference to FIG. 3, step 24 of this embodiment includes the following sub-steps. In sub-step S241, a plurality of values are determined from the images captured in step S23. Each of the values is representative of the number of pixels having a grayscale level that falls within a predefined range in a corresponding one of the images captured in step S23. In sub-step S242, a mean of the values determined in sub-step S241 is determined so as to obtain the second feature parameter.

According to this embodiment, in step 25, the difference between the first and second feature parameters is determined to have statistical significance when the second feature parameter is smaller than the first feature parameter and when a p-value resulting from the difference is smaller than 0.05.

Figure 4:
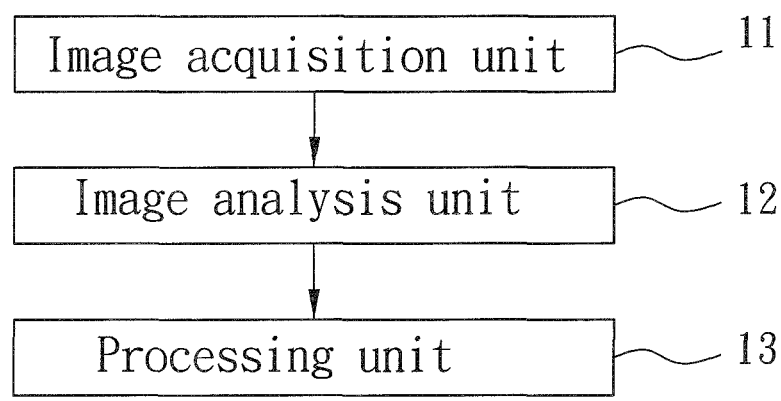
FIG. 4 is a block diagram, illustrating the preferred embodiment of a system for screening of a to-be-analyzed candidate as a skin-whitening agent according to the present invention.

According to another aspect of the present invention, with reference to FIG. 4, the preferred embodiment of a system for screening of a to-be-analyzed candidate as a skin-whitening agent includes an image acquisition unit 11, an image analyzing unit 12, and a processing unit 13. The image acquisition unit 11 is for acquiring images of zebrafish of first and second groups. The first group of zebrafish is bred under a predetermined set of breeding conditions. The second group of zebrafish is bred under the predetermined set of breeding conditions and is administered with the to-be-analyzed candidate during the breeding process. The image analyzing unit 12 is for determining, from the images acquired by the image acquisition unit 11, a first feature parameter corresponding to the first group of zebrafish and a second feature parameter corresponding to the second group of zebrafish. The processing unit 13 is for concluding that the to-be-analyzed candidate is suitable as a skin-whitening agent if a difference between the first and second feature parameters has statistical significance.

Preferably, the image acquisition unit 11 is a microscope that is equipped with a digital camera. Examples of the microscope include: stereomicroscope, fluorescence stereomicroscope, macroscope, upright optical microscope, inverted optical microscope, fluorescence microscope, upright fluorescence microscope, inverted fluorescence microscope, dissecting fluorescence microscope, upright microscope, inverted microscope, polarizing microscope, dissecting microscope, and biomicroscope. It should be noted herein that operation of the microscope varies with factors such as the type and model number of the microscope and other peripheral equipments, and should fall within the knowledge of a person with ordinary skill in the art. Therefore, further details of the same are omitted herein for the sake of brevity.

Preferably, the microscope is a stereomicroscope, such as Leica Z16 APO stereomicroscope (Leica Microsystems), Motic K Series stereomicroscope model no. K-500 (Motic Group Co. Ltd.), Leica M205A stereomicroscope (Leica Microsystems), and Leica MZ6 modular stereomicroscope (Leica Microsystems).

In this embodiment, the image acquisition unit 11 is implemented using one of Leica Z16 APO stereomicroscope that is equipped with SPOT Idea™ digital camera (SPOT™ Imaging Solutions, U.S.A.) and Motic K Series stereomicroscope model no. K-500 that is equipped with MOTICAM 1000 live imaging microscopy camera (Motic Group Co. Ltd.).

Preferably, the image analyzing unit 12 determines, from the images acquired by the image acquisition unit 11, a plurality of values, each of which is representative of the number of pixels having a grayscale level that falls within a predefined range in a corresponding one of the images, and further determines a mean of the values thus determined for the first group of zebrafish so as to obtain the first feature parameter, and a mean of the values thus determined for the second group of zebrafish so as to obtain the second feature parameter.

In this embodiment, the image analyzing unit 12 is implemented using an image analysis software, such as Image Scion (Scion Corporation, U.S.A.), ImageJ version 1.40 g (ImageJ, National Institute of Health, Bethesda, Md., U.S.A.), LAS Image Analysis software module (Leica), Leica IM1000 (Leica), Leica QWIN image analysis and processing solution (Leica), AxioVision digital image processing software (Zeiss), Image-Pro Plus® (MediaCybernetics®), MetaMorph® Research Imaging Software (Molecular Devices®), NIS-Elements AR (Advanced Research) imaging software (Nikon), NIS-Elements BR (Basic Research) imaging software (Nikon), MetaVue™ Research Imaging Software (Molecular Devices®), Universal Imaging Utility (Binary Research International Inc.), Optimas® (Meyer Instruments Inc.), Imatest Master (Imatest), etc.

To the applicant's knowledge, the above-listed image analysis software are currently mainly used for cancer drug development, cancer cell form analysis and proteomic analysis. Furthermore, it should be noted herein that operation of the image analysis software varies with factors such as the model number of the image analysis software and other peripheral equipment and settings, and should fall within the knowledge of a person of ordinary skill in the art. Therefore, further details of the same are omitted herein for the sake of brevity.

In this embodiment, the image analyzing unit 12 is implemented using one of Image Scion (Scion Corporation, U.S.A.) with an upper index value of 254 and a lower index value of 150 for defining the predefined range, and ImageJ version 1.40 g (ImageJ, National Institute of Health, Bethesda, Md., U.S.A.) with an upper threshold value of 85 and a lower threshold value of 0 for defining the predefined range. In addition, the pixel having a grayscale level that falls within the predefined range is considered to be a "valid pixel", and the value determined for a particular image is considered to be the "total number of valid pixels" in the image corresponding to a particular zebrafish.

Moreover, it should be noted herein that different image acquisition units 11 may be used with different image analyzing units 12.

In this embodiment, the processing unit 13 determines that the difference between the first and second feature parameters has statistical significance when the second feature parameter is smaller than the first feature parameter (indicating that the skin color of the zebrafish administered with the to-be-analyzed candidate is brighter/whiter than the natural skin color of the zebrafish) and when a p-value resulting from the difference is smaller than 0.05.

The applicant conducted several experiments to verify the reliability of the method and system of the present invention. The experiments were conducted using the following chemicals and preparation procedures.

A. Materials Used During Experimentation:

1. The formula of the Hank's buffer used in the experiments is listed in Table 1 below.

TABLE 1

| Composition | Concentration (mg/mL) |
|---|---|
| KCl | 0.2 |
| $Na_2HPO_4$ | 1.42 |
| $KH_2PO_4$ | 0.24 |
| NaCl | 8 |
| $NaHCO_3$ | 0.175 |
| $CaCl_2$ | 0.72 |
| $MgSO_4$ | 1.23 |

The rest is deionized water

2. Zebrafish embryos were prepared as follows.

The zebrafish (AB strain) serving as parent fish were purchased from Taikong Corp., Taiwan. The male fish and the female fish were separately raised in two water tanks with sufficient feed under a controlled water temperature of 28.5 degrees Celsius, and a controlled light-dark cycle of 14 hours of light and 10 hours of darkness.

The preparation of the zebrafish embryos was similar to, but with small modifications from, that disclosed in M. Westerfield (2007), *The Zebrafish Book: A Guide for the Laboratory Use of Zebrafish (Danio Rerio)*, 5th edit. University of Oregon Press, Eugene, Oreg. First, one female fish and two male fish were put in a breeding tank having an acrylic grid under a water temperature of 28.5 degrees Celsius. Then, the breeding tank was made to undergo a first light-dark cycle of 14 hours of light and 10 hours of darkness. Subsequently, during the second light-dark cycle, the female fish and the male fish would respectively produce eggs and sperms for fertilization so as to obtain fertilized eggs. These fertilized eggs are referred to as fertilized eggs from "the same parental generation". Next, after an hour, the fertilized eggs were removed from the breeding tank with a dropper, and were disposed in a Petri dish containing the Hank's buffer prepared according to the above-disclosed formula. Later, the Petri dish was disposed in an incubator (RI-80, FIRSTEK, Taiwan) under a controlled temperature of 28.5 degrees Celsius, and a controlled light-dark cycle of 14 hours of light and 10 hours of darkness for a 9-hour breeding process to allow development of the fertilized eggs into embryos. Subsequently, a Leica Z16 APO stereomicroscope (Leica, Heerbrugg, Switzerland) was used for the observation of the development of various embryos. Based on the observations, only well-developed embryos were kept for use in the experiments that followed.

Zebrafish coming from "different parental generations" were bred in the same manner with different groups of female and male zebrafish.

B. Methods & Equipments Used During Experimentation

1. Statistical analysis

For the experiments, a statistical analysis software called Sigma Stat (2.03 version) for Windows® was used for statistical analysis. The experimental data was represented in terms of mean+/−SEM (standard error of the mean). The analysis was conducted using one-way analysis of variance (ANOVA) followed by Duncan's method so as to evaluate the difference between different sets of data. When the difference between different sets of data results in a p-value of smaller than 0.05, statistical significance is established.

2. Image acquisition unit was implemented using one of the following stereomicroscopes.
(1) Leica Z16 APO stereomicroscope (Leica, Heerbrugg, Switzerland) equipped with a SPOT Idea™ digital camera (SPOT™ Imaging Solutions, U.S.A.)
(2) Motic K Series stereomicroscope model no. K-500 (Motic Group Co. Ltd.), equipped with MOTICAM 1000 live imaging microscopy camera (Motic Group Co. Ltd.) and Motic Image Plus 2.0 software.

3. Image analyzing unit was implemented using one of the following software.
(1) Image Scion (Scion Corporation, U.S.A.) with operation parameters set in Table 2 below for defining the predefined range for a pixel to be considered as a "valid pixel".

TABLE 2

| Operation parameter | Set value |
| --- | --- |
| Upper index value | 254 |
| Lower index value | 150 |

(2) ImageJ version 1.40 g (ImageJ, National Institute of Health, Bethesda, Md., U.S.A.) with operation parameters set in Table 3 below for defining the predefined range for a pixel to be considered a "valid pixel".

TABLE 3

| Operation parameter | Set value |
| --- | --- |
| Upper threshold value | 85 |
| Lower threshold value | 0 |

C. Results Obtained Through Experimentation

Figure 5:
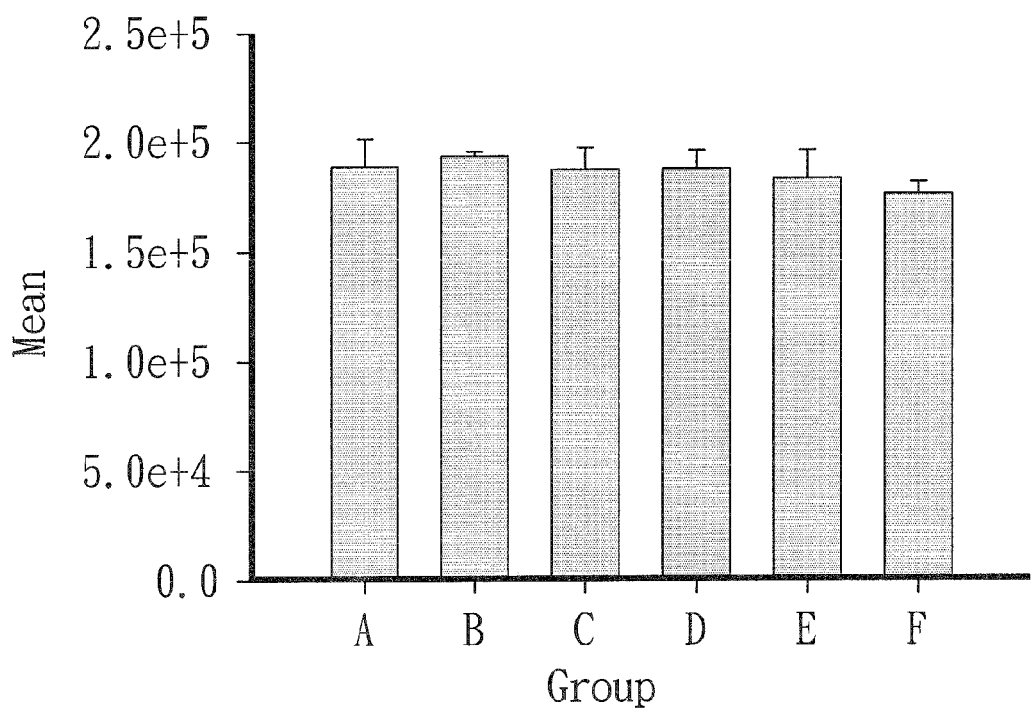
FIG. 5 is a bar graph, illustrating experimental results of six groups of zebrafish coming from the same parental generation for determining if inter-individual difference exists in the natural skin color of zebrafish larvae coming from the same parental generation (with data represented in terms of mean+/−SEM (standard error of the mean))

After experimentation, the applicant found that inter-individual difference does not exist in the natural skin color of zebrafish larvae coming from the same parental generation. During the experiment, a plurality of zebrafish larvae coming from the same parental generation were randomly grouped into six groups (A~F). Image Scion was used as the image analyzing unit 12 (shown in FIG. 4) to obtain a plurality of values, each representative of the number of "valid pixels" in an image for a corresponding zebrafish larva. Each bar in FIG. 5 shows a mean of the values for a corresponding group (A~F) (i.e., average number of valid pixels in the zebrafish larvae of the corresponding group (A~F)). The differences among these means for the six groups (A~F) show no statistical significance. It is therefore concluded that inter-individual difference does not exist in the natural skin color of zebrafish larvae coming from the same parental generation.

Figure 6:
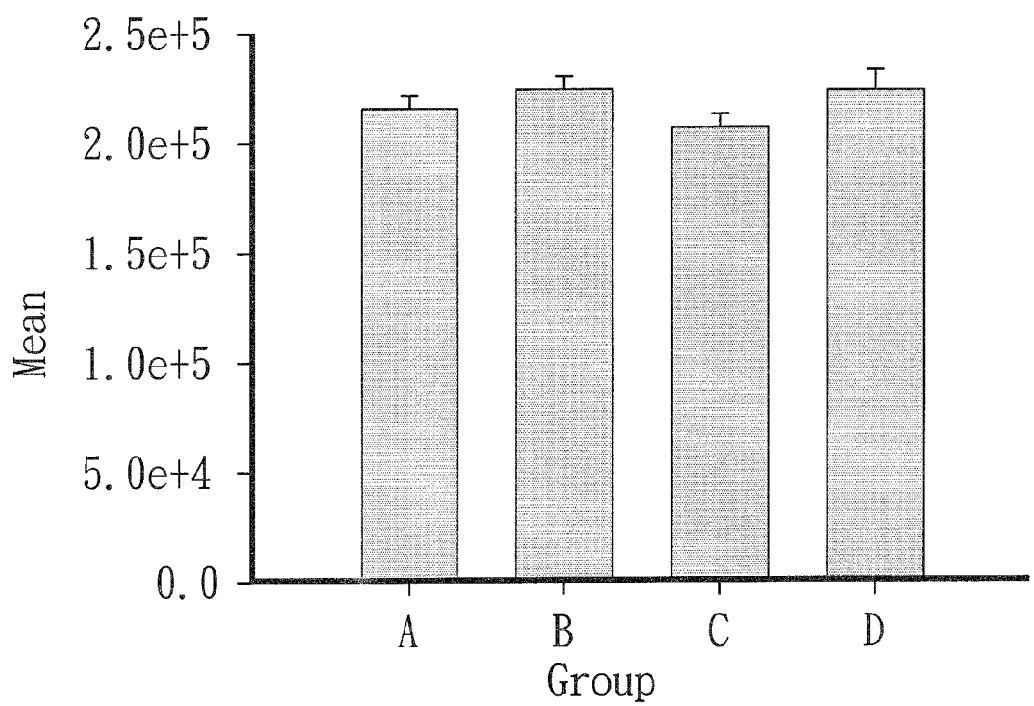
FIG. 6 is a bar graph, illustrating experimental results of four groups of zebrafish respectively coming from four different parental generations for determining if inter-individual difference exists in the natural skin color of zebrafish larvae coming from different parental generations (with data represented in terms of mean+/−SEM)

Similarly, after another experimentation using Image Scion, the applicant found that inter-individual difference does not exist in the natural skin color of zebrafish larvae coming from different parental generations. Four groups (A~D) of zebrafish larvae, each coming from a different parental generation, were used for the experiment. The results are shown in FIG. 6, with each bar representing average number of valid pixels for the zebrafish larvae of a corresponding group. The differences among these averages for the four groups (A~D) show no statistical significance. Therefore, it is concluded that inter-individual difference does not exist in the natural skin color of zebrafish larvae coming from different parental generations.

Figure 7A:
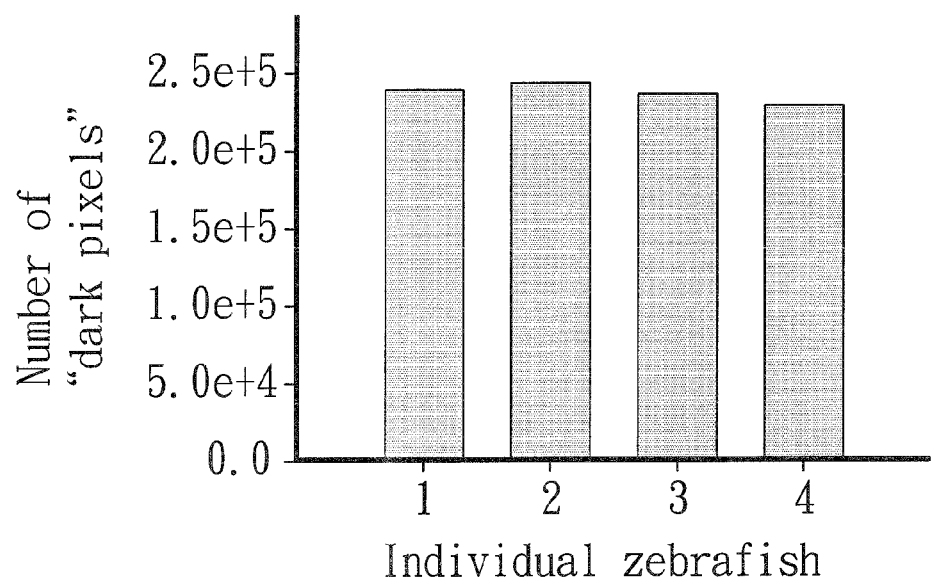
FIGS. 7A and 7B are bar graphs, each illustrating experimental results of the same four individual zebrafish that were analyzed using a corresponding one of two different image acquisition units (with data represented in terms of mean+/−SEM)
Figure 7B:
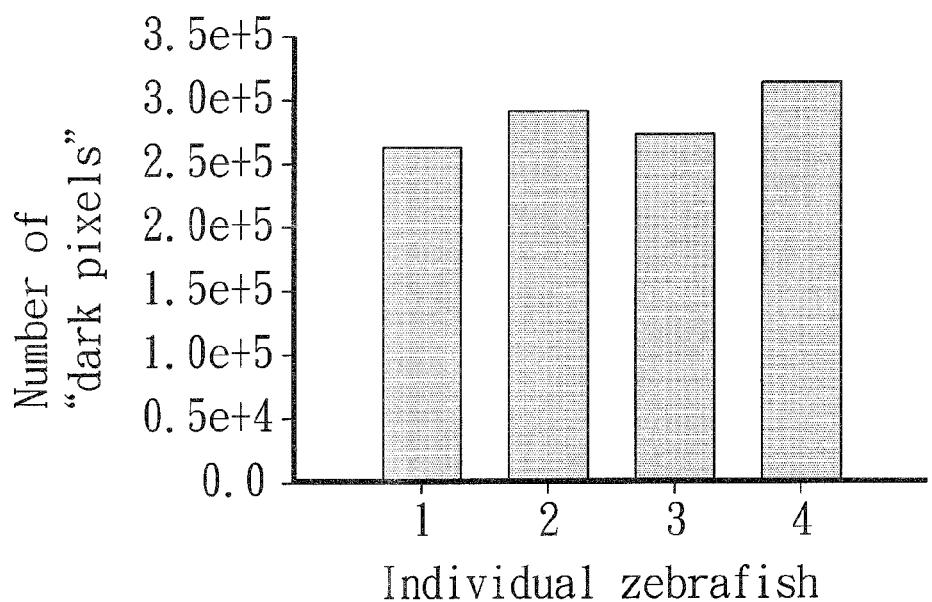

The applicant also conducted a further experiment to assess whether different image acquisition units 11 (shown in FIG. 4) would generate statistically significant different results. During the experiment, images of four individual zebrafish were captured using each of the stereomicroscopes listed under sub-section 3 of section B (Methods & Equipments used during experimentation) above (i.e., eight images were captured in total). For each of the eight images, the number of "valid pixels" was determined. Shown in FIG. 7A are the results corresponding to the images captured by the first stereomicroscope listed under sub-section 3 of section B, and shown in FIG. 7B are the results corresponding to the images captured by the second stereomicroscope listed under sub-section 3 of section B. After statistical analysis, the difference between the results shown in FIGS. 7A and 7B do not show statistical significance. Thus, different implementations of the image acquisition unit 11 (shown in FIG. 4) do not affect the outcome.

Figure 8A:
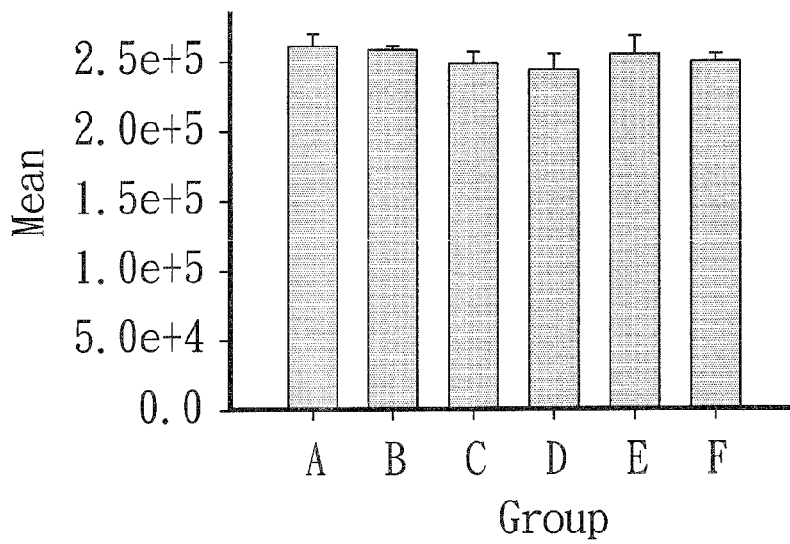
FIGS. 8A, 8B and 8C are bar graphs, each illustrating experimental results of the same six groups of zebrafish that came from the same parental generation and that were analyzed using Image Scion with a lower index value set to a corresponding one of three values (with data represented in terms of mean+/−SEM)
Figure 8B:
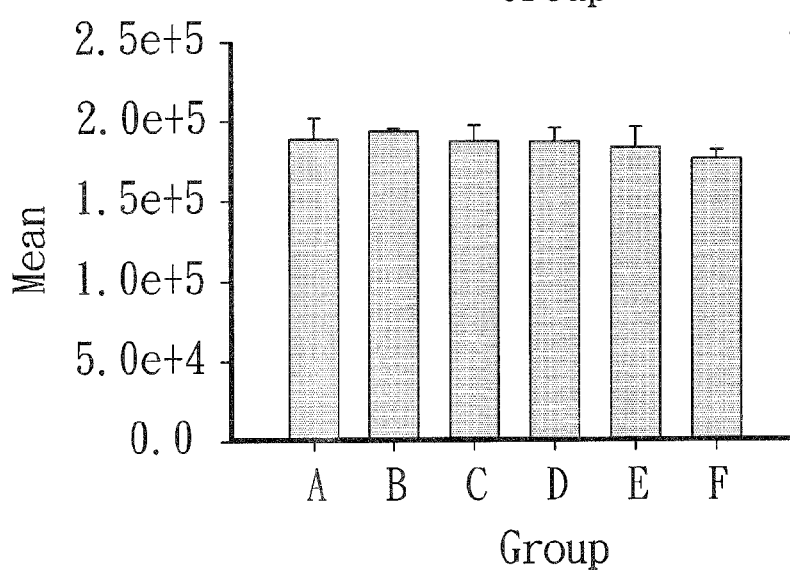
Figure 8C:
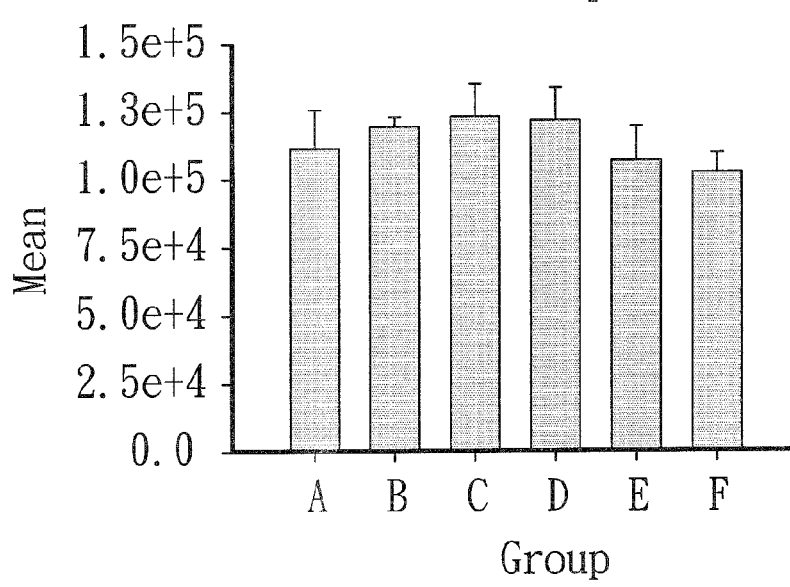
Figure 9A:
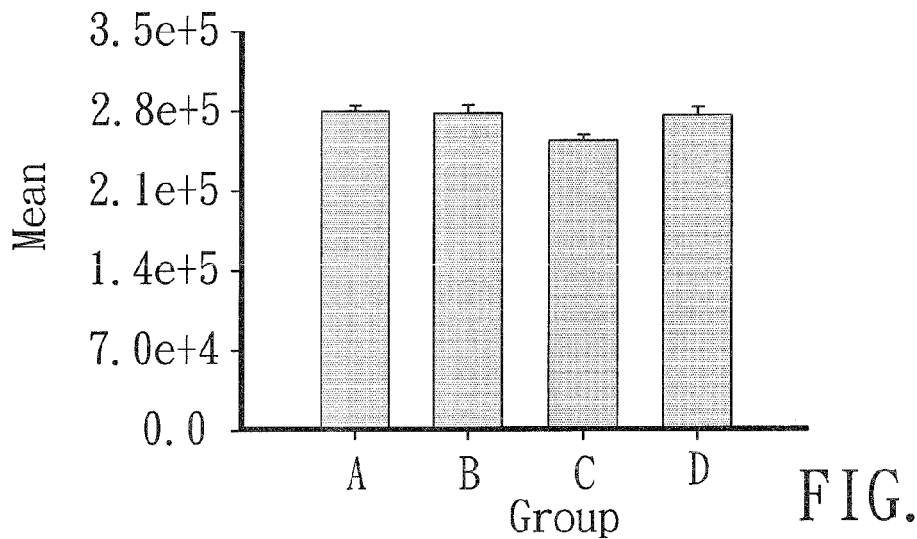
FIGS. 9A, 9B and 9C are bar graphs, each illustrating experimental results of the same four groups of zebrafish that came from four different parental generations and that were analyzed using Image Scion with a lower index value set to a corresponding one of three values (with data represented in terms of mean+/−SEM)
Figure 9B:
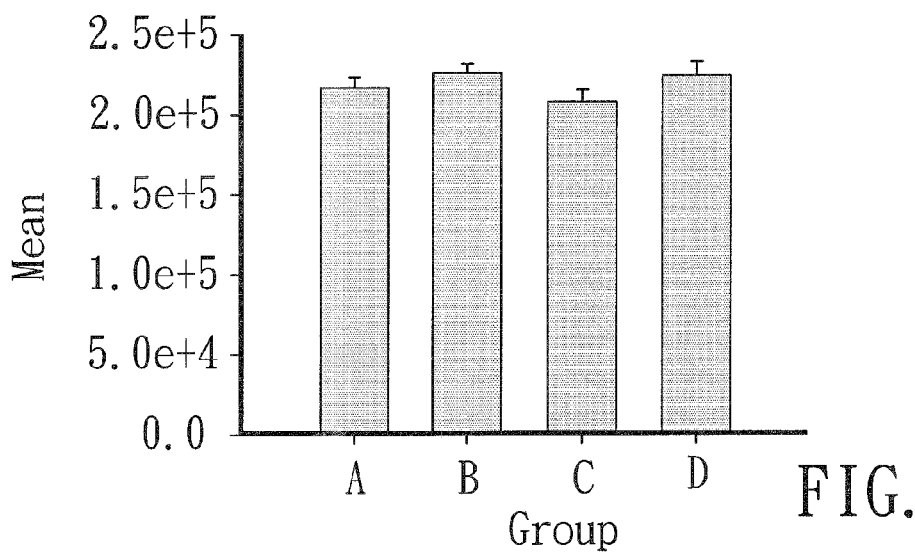
Figure 9C:
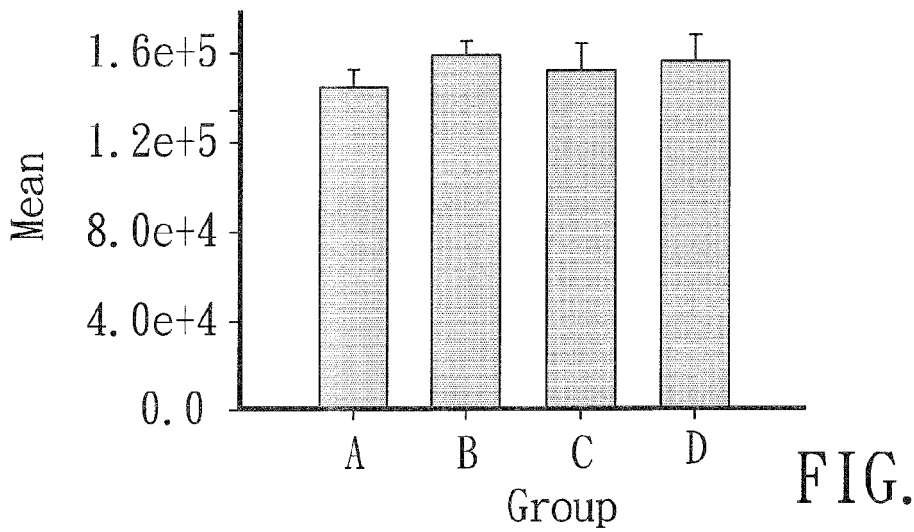

Moreover, the applicant conducted an additional experiment to determine whether the lower index value of Image Scion would affect the results, the lower index value defining a lower boundary of the predefined range. Shown in FIGS. 8A, 8B and 8C are results obtained for zebrafish coming from the same parental generation using Image Scion as the image analyzing unit 12 by respectively setting the lower index value at 120, 150 and 180. Shown in FIGS. 9A, 9B and 9C are results obtained for zebrafish coming from different parental generations using Image Scion as the image analyzing unit 12 by respectively setting the lower index value at 120, 150 and 180. After statistical analysis, it was shown that no statistical significance exists in the differences resulting from different lower index values, both for the zebrafish coming from the same parental generation and coming from different parental generations.

Figure 10A:
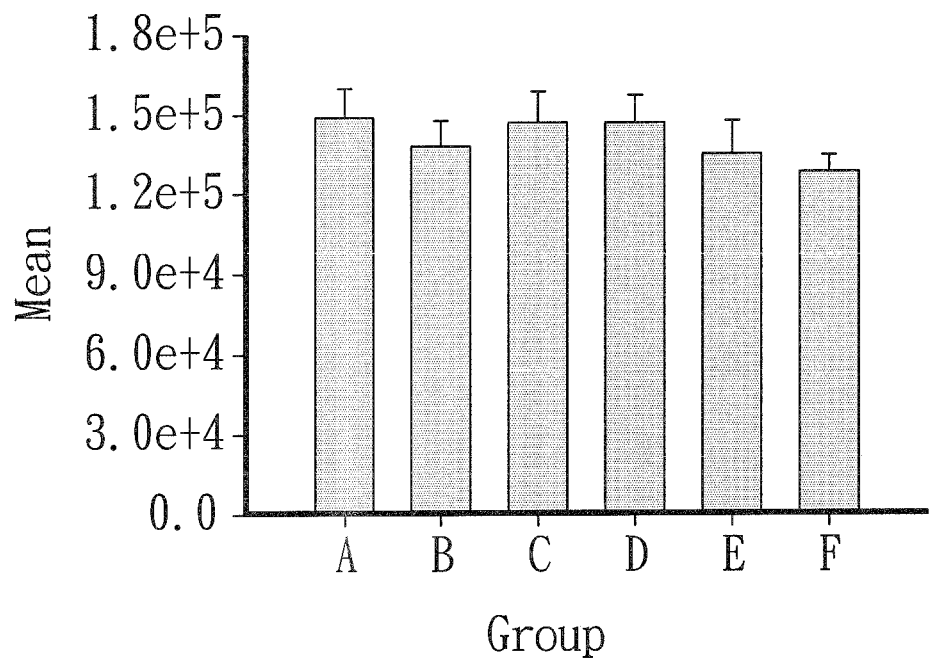
FIG. 10A is a bar graph, illustrating experimental results of the six groups of zebrafish as in FIG. 5 using ImageJ version 1.40 g as an image analyzing unit (with data represented in terms of mean+/−SEM)
Figure 10B:
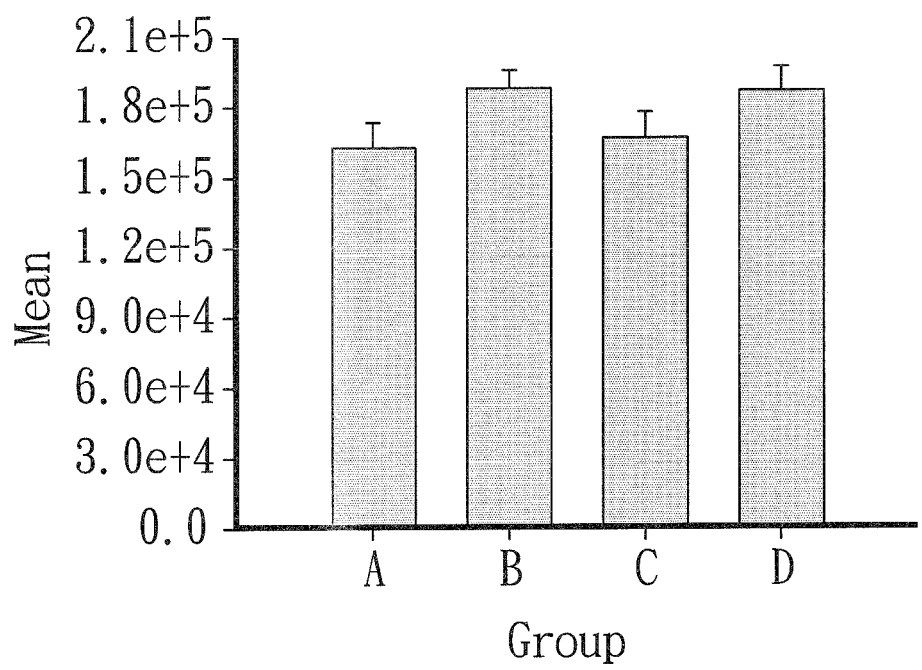
FIG. 10B is a bar graph, illustrating experimental results of the four groups of zebrafish as in FIG. 6 using ImageJ version 1.40 g as an image analyzing unit (with data represented in terms of mean+/−SEM)

Another experimentation was conducted to determine whether different image analyzing units 12 (shown in FIG. 4) would generate statistically significant different results. The results obtained using ImageJ version 1.40 g as the image analyzing unit 12 for the same groups of zebrafish used for one of the previously described experiments, whose results are shown in FIG. 5 and were obtained using Image Scion as the image analyzing unit 12, are illustrated in FIG. 10A. The results obtained using ImageJ version 1.40 g as the image analyzing unit 12 for the same groups of zebrafish used for another previously described experiment, whose results are shown in FIG. 6 and were obtained using Image Scion as the image analyzing unit 12, are illustrated in FIG. 10B. The differences between the results of FIGS. 5 and 10A, and the differences between the results of FIGS. 6 and 10B show no statistical significance. Therefore, it is concluded that different implementations of the image analyzing unit 12 does not affect the outcome.

It can thus be verified from the above experiments that the method and system for screening of a to-be-analyzed candidate as a skin-whitening agent according to the present invention is not affected by the differences between individual zebrafish, whether from the same parental generations or different parental generations, nor is it affected by the differences in the implementations of the image acquisition unit 11 and the image analyzing unit 12.

In order to further verify the effectiveness of the method and system for screening of a to-be-analyzed candidate as a skin-whitening agent according to the present invention, the applicant conducted the following experiments to test three known skin-whitening agents. In particular, arbutin, N-phenylthiourea (PTU) and kojic acid were used as the to-be-analyzed candidates for verification of effectiveness of the present invention.

Experimentation Procedures

Procedure A. Administration of Different to-be-Analyzed Candidates of Different Concentrations to Zebrafish Embryos First, arbutin (Sigma, Cat. No. A4256), N-phenylthiourea (Sigma, Cat. No. P7629) and kojic acid (Sigma, Cat. No. K3125) were respectively dissolved in a 2% dimethyl sulfoxide (DMSO) solution prepared from Hank's buffer to result in arbutin solutions with concentrations of 0.1 mM, 0.2 mM, 1 mM, 2 mM, 10 mM and 20 mM, N-phenylthiourea solutions with concentrations of 0.002 mM, 0.02 mM, 0.2 mM, 0.4 mM, 1 mM and 2 mM, and kojic acid solutions with concentrations of 0.2 mM, 1 mM, 2 mM, 20 mM, 40 mM and 100 mM, respectively. Next, each well of a 96-well plate is provided with 100 µL of Hank's buffer. Subsequently, in accordance with the operational conditions set forth below in Table 4, the zebrafish prepared in the way previously described under subsection 2 of section A (Materials used during experimentation) were added respectively to the wells, to which 100 µL of the to-be-analyzed candidates, i.e., arbutin, N-phenylthiourea and kojic acid solutions of various concentrations, were added so as to result in the final concentrations as shown in Table 4. The 96-well plate was then disposed in an incubator under a controlled temperature of 28.5 degrees Celsius, and a controlled light-dark cycle of 14 hours of light and 10 hours of darkness for a 48-hour breeding period to allow the embryos to develop into zebrafish larvae. It should be noted herein that the above procedure was for preparation of a plurality of the "second groups of zebrafish" (i.e., test groups (A2~A7, N2~N7, K2~K7)), while each of the "first groups of zebrafish" (each for a kind of the to-be-tested candidate) were prepared using the same breeding process without the administration of the to-be-analyzed candidates so as to form control groups (A1, N1, K1).

TABLE 4

| Group No. | To-be-analyzed candidate Type | Final Concentration (mM) | Number of Zebrafish in Group |
|---|---|---|---|
| A1 | Arbutin | 0 | 6 |
| A2 | Arbutin | 0.05 | 7 |
| A3 | Arbutin | 0.1 | 6 |
| A4 | Arbutin | 0.5 | 7 |
| A5 | Arbutin | 1 | 11 |
| A6 | Arbutin | 5 | 8 |
| A7 | Arbutin | 10 | 5 |
| N1 | N-phenylthiourea | 0 | 19 |
| N2 | N-phenylthiourea | 0.001 | 24 |
| N3 | N-phenylthiourea | 0.01 | 25 |
| N4 | N-phenylthiourea | 0.1 | 21 |
| N5 | N-phenylthiourea | 0.2 | 21 |
| N6 | N-phenylthiourea | 0.5 | 20 |

TABLE 4-continued

| Group No. | To-be-analyzed candidate Type | Final Concentration (mM) | Number of Zebrafish in Group |
|---|---|---|---|
| N7 | N-phenylthiourea | 1 | 21 |
| K1 | kojic acid | 0 | 19 |
| K2 | kojic acid | 0.1 | 9 |
| K3 | kojic acid | 0.5 | 6 |
| K4 | kojic acid | 1 | 8 |
| K5 | kojic acid | 10 | 24 |
| K6 | kojic acid | 20 | 25 |
| K7 | kojic acid | 50 | 15 |

Procedure B. Acquisition of Images of the Zebrafish

A tricaine methanesulfonate solution (MS-222) with a concentration of 168 ppm was used to anesthetize the zebrafish larvae prepared in Procedure A. Next, a depression slide (Micro Scientific Laboratories, Inc., U.S.A., Cat. No. MM-104SC) containing 1% methyl cellulose (Sigma, Cat. No. M0512) was used to mount the zebrafish. Subsequently, Leica Z16 APO stereomicroscope was used to acquire images of the zebrafish with a 25× magnification rate and a 3.372 ms exposure time.

Procedure C. Analysis of Images of the Zebrafish

Image Scion was used to determine the mean of the number of "valid pixels" (i.e., pixels whose grayscale levels fall within a predefined range) in the images corresponding to the zebrafish of the same group. For each of the control groups (A1, N1, K1) of zebrafish, the mean represents the first feature parameter of the corresponding one of the to-be-analyzed candidates, i.e., arbutin, N-phenylthiourea and kojic acid solutions. For each of the test groups (A2~A7, N2~N7, K2~K7) of zebrafish, the mean represents the second feature parameter of the corresponding one of the to-be-analyzed candidates, i.e., arbutin, N-phenylthiourea and kojic acid solutions at a corresponding concentration.

Procedure D. Analysis of the Difference Between First and Second Feature Parameters Sigma Stat (2.03 version) for Windows® was used for the statistical analysis, i.e., to determine if a difference between each pair of the first and second feature parameters has statistical significance by determining a p-value based on the difference when the second feature parameter is smaller than the first feature parameter. When the p-value is smaller than 0.05, it is concluded that the difference has statistical significance, and that the to-be-analyzed candidate is suitable as a skin-whitening agent. The experiment data was represented in terms of mean+/−SEM (standard error of the mean). The analysis was conducted using one-way analysis of variance (ANOVA) followed by Duncan's method so as to evaluate the difference between different sets of data.

Results

Figure 11:
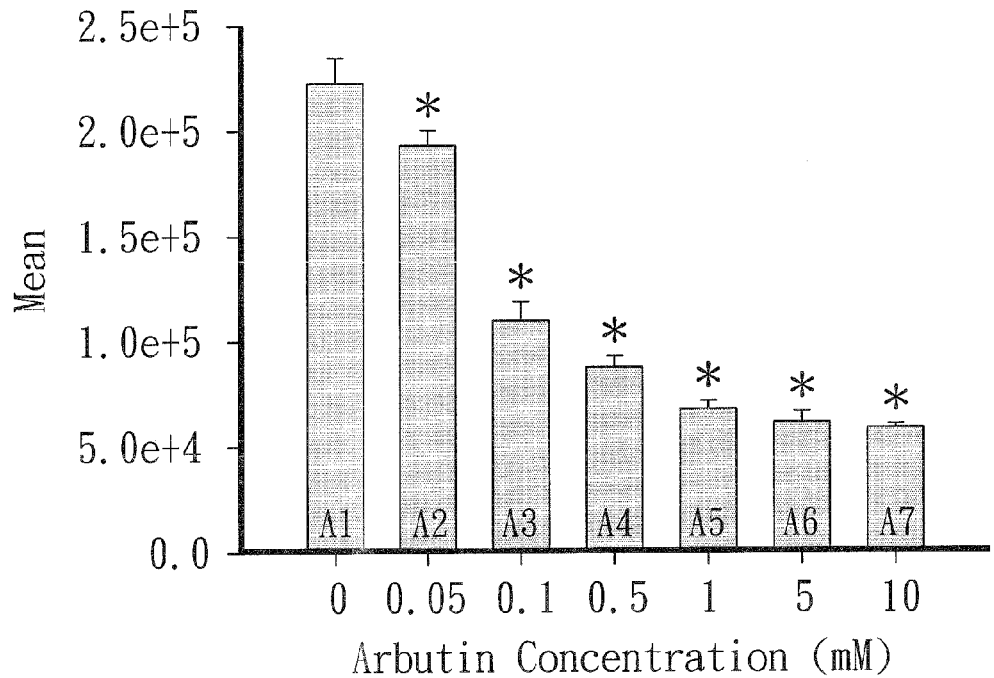
FIG. 11 is a bar graph, illustrating experimental results of seven groups (A1~A7) of zebrafish for the screening of arbutin as a skin-whitening agent using the method and system according to the present invention with the image analyzing unit implemented using Image Scion.
Figure 12:
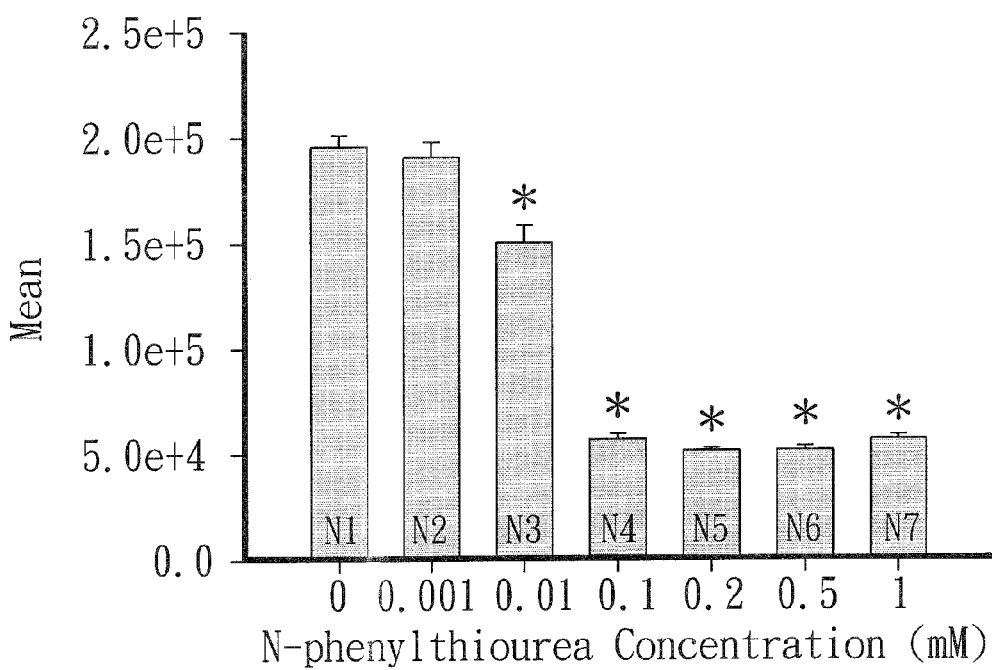
FIG. 12 is a bar graph, illustrating experimental results of seven groups (N1~N7) of zebrafish for the screening of N-phenylthiourea as a skin-whitening agent using the method and system according to the present invention with the image analyzing unit implemented using Image Scion.

Each bar shown in FIG. 11 represents the mean obtained for a corresponding group (A1~A7) of zebrafish used for the screening of arbutin as a skin-whitening agent. Each bar shown in FIG. 12 represents the mean obtained for a corresponding group (N1~N7) of zebrafish used for the screening of N-phenylthiourea as a skin-whitening agent. Each bar shown in FIG. 13 represents the mean obtained for a corresponding group (K1~K7) of zebrafish used for the screening of kojic acid as a skin-whitening agent.

Figure 13:
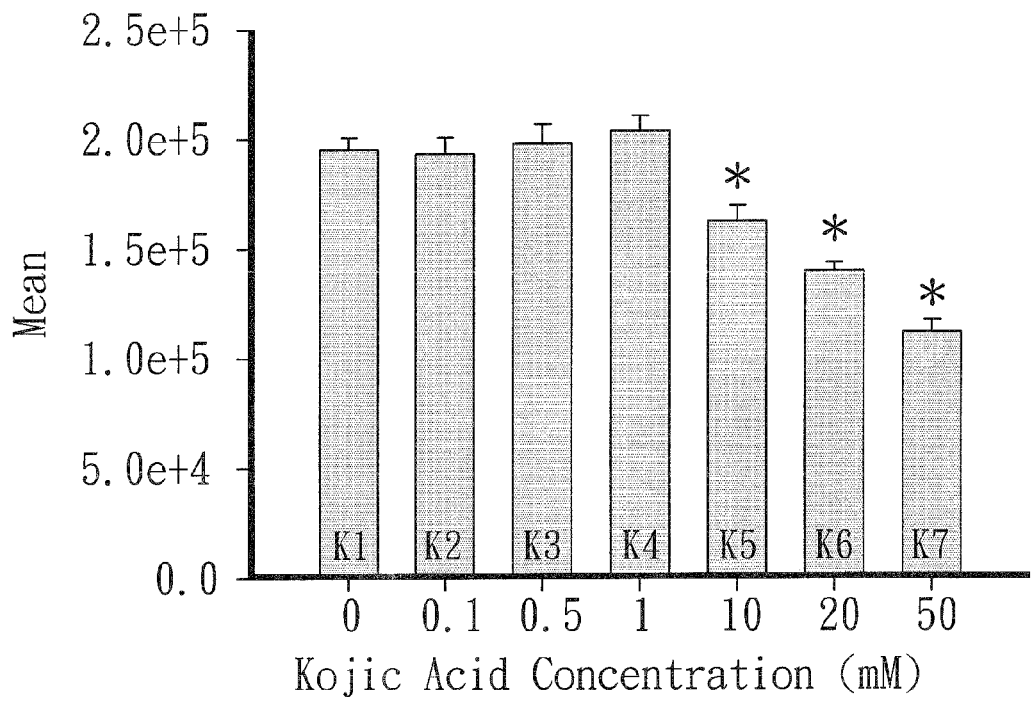
FIG. 13 is a bar graph, illustrating experimental results of seven groups (K1~K7) of zebrafish for the screening of kojic acid as a skin-whitening agent using the method and system according to the present invention with the image analyzing unit implemented using Image Scion.

It is evident from FIGS. 11, 12 and 13 that, for each of the to-be-analyzed candidates, i.e., arbutin, N-phenylthiourea and kojic acid, the mean of the number of "valid pixels" decreases with the concentration of the administered to-be-analyzed candidates. Moreover, a "*" symbol is marked on each bar, the difference of the corresponding second feature parameter of which is smaller than the first feature parameter for the same to-be-analyzed candidate and demonstrates statistical significance. As shown in FIG. 11, the bar corresponding to each of the test groups (A2~A7) of zebrafish is marked with the "*" symbol, indicating that there is statistical significance in the difference between the skin color of the test group (A2~A7) and the control group (A1). This is evidence that the reduction of "valid pixels" in the images of the zebrafish was the result of the administration of arbutin having the concentration of at least 0.05 mM. Similarly, as shown in FIG. 12, the bar corresponding to each of the test groups (N3~N7) of zebrafish is marked with the "*" symbol, indicating that there is statistical significance in the difference between the skin color of the test group (N3~N7) and the control group (N1). This is evidence for concluding that the reduction of "valid pixels" in the images of the zebrafish was the result of the administration of N-phenylthiourea having the concentration of at least 0.01 mM. As shown in FIG. 13, the bar corresponding to each of the test groups (K5~K7) of zebrafish is marked with the "*" symbol, indicating that there is statistical significance in the difference between the skin color of the test group (K5~K7) and the control group (K1). This means that the reduction of "valid pixels" in the images of the zebrafish was the result of the administration of kojic acid having the concentration of at least 10 mM.

With reference to the above, the experiment results demonstrated that arbutin, N-phenylthiourea and kojic acid are all suitable as skin-whitening agents. In addition, it is also verified through the above experimentation that the method and system for screening of a to-be-analyzed candidate as a skin-whitening agent according to the present invention are effective in assessing and screening of various kinds of to-be-analyzed candidates.

Figure 14:
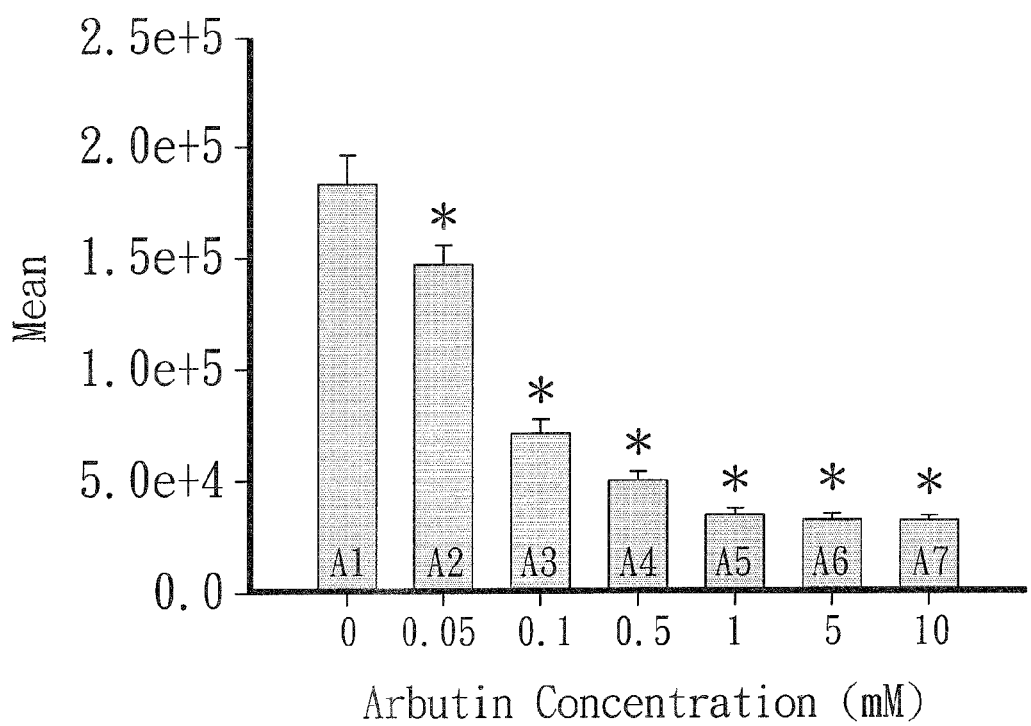
FIG. 14 is a bar graph, illustrating experimental results of seven groups (A1~A7) of zebrafish for the screening of arbutin as a skin-whitening agent using the method and system according to the present invention with the image analyzing unit implemented using ImageJ version 1.40 g.

In order to further verify that the results would not be affected when the images captured by the same image acquisition unit 11 (shown in FIG. 4) are analyzed using a different image analyzing unit 12 (shown in FIG. 4), the applicant further performed Procedure C using ImageJ version 1.40 g on the images captured for the groups (A1~A7) of zebrafish used for the screening of arbutin as a skin-whitening agent, the results of which are illustrated in FIG. 14. By comparing FIG. 11 and FIG. 14, it is evident that there is no significant difference between the results obtained using Image Scion and ImageJ version 1.40 g as the image analyzing unit 12. Therefore, it is also concluded herein that the present invention is not affected by the implementation of the image analyzing unit 12.

In summary, the present invention provides a method and a system for screening of a to-be-analyzed candidate as a skin-whitening agent that provides accurate and objective, statistically significant results.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for screening of a to-be-analyzed candidate as a skin-whitening agent, the method comprising the steps of:
   (a) setting a first feature parameter corresponding to a first group of zebrafish that are bred under a predetermined set of breeding conditions;
   (b) administering the to-be-analyzed candidate to a second group of zebrafish that are bred under the predetermined set of breeding conditions;
   (c) capturing images of the zebrafish in the second group;
   (d) determining, from the images captured in step (c), a second feature parameter corresponding to the second group of zebrafish; and
   (e) concluding that the to-be-analyzed candidate is suitable as a skin-whitening agent if a difference between the first and second feature parameters has statistical significance.

2. The method as claimed in claim 1, wherein step (a) includes the sub-steps of:
   (a-1) capturing images of the zebrafish in the first group;
   (a-2) determining, from the images captured in sub-step (a-1), a plurality of values, each of which is representative of the number of pixels having a grayscale level that falls within a predefined range in a corresponding one of the images; and
   (a-3) determining a mean of the values determined in sub-step (a-2) so as to obtain the first feature parameter.

3. The method as claimed in claim 2, wherein step (d) includes the sub-steps of:
   (d-1) determining, from the images captured in step (c), a plurality of values, each of which is representative of the number of pixels having a grayscale level that falls within a predefined range in a corresponding one of the images; and
   (d-2) determining a mean of the values determined in sub-step (d-1) so as to obtain the second feature parameter.

4. The method as claimed in claim 3, wherein, in step (e), the difference between the first and second feature parameters is determined to have statistical significance when the second feature parameter is smaller than the first feature parameter and when a p-value resulting from the difference is smaller than 0.05.

5. The method as claimed in claim 1, wherein in step (e), the difference between the first and second feature parameters is determined to have statistical significance when a p-value resulting from the difference is smaller than 0.05.

6. The method as claimed in claim 1, wherein step (c) is implemented using a microscope that is equipped with a digital camera.

7. A system for screening of a to-be-analyzed candidate as a skin-whitening agent, comprising:
   an image acquisition unit for acquiring images of zebrafish of first and second groups, the first group of zebrafish being bred under a predetermined set of breeding conditions, the second group of zebrafish being bred under the predetermined set of breeding conditions and being administered with the to-be-analyzed candidate during the breeding process;
   an image analyzing unit for determining, from the images acquired by said image acquisition unit, a first feature parameter corresponding to the first group of zebrafish and a second feature parameter corresponding to the second group of zebrafish, wherein said image analyzing unit is a processor; and
   a processing unit for concluding that the to-be-analyzed candidate is suitable as a skin-whitening agent if a difference between the first and second feature parameters has statistical significance, wherein said processing unit is a processor.

8. The system as claimed in claim 7, wherein said image analyzing unit determines, from the images acquired by said image acquisition unit, a plurality of values, each of which is representative of the number of pixels having a grayscale level that falls within a predefined range in a corresponding one of the images, and further determines a mean of the values thus determined for the first group of zebrafish so as to obtain the first feature parameter, and a mean of the values thus determined for the second group of zebrafish so as to obtain the second feature parameter.

9. The system as claimed in claim 8, wherein, said processing unit determines the difference between the first and second feature parameters to have statistical significance when the second feature parameter is smaller than the first feature parameter and when a p-value resulting from the difference is smaller than 0.05.

10. The system as claimed in claim 7, wherein said processing unit determines the difference between the first and second feature parameters to have statistical significance when a p-value resulting from the difference is smaller than 0.05.

11. The system as claimed in claim 7, wherein said image acquisition unit is a microscope that is equipped with a digital camera.

* * * * *